USOO5750100A

United States Patent [19]
Yamagata et al.

[11] Patent Number: 5,750,100
[45] Date of Patent: *May 12, 1998

[54] SUSTAINED RELEASABLE PARENTERAL PHARMACEUTICAL PREPARATIONS AND METHOD OF PRODUCING THE SAME

[75] Inventors: Yutaka Yamagata, Kobe; Katsumi Iga; Hiroaki Okada, both of Suita, all of Japan

[73] Assignee: Takeda Chemical Industries, Ltd., Osaka, Japan

[*] Notice: The term of this patent shall not extend beyond the expiration date of Pat. No. 5,628,993.

[21] Appl. No.: 734,636

[22] Filed: Oct. 21, 1996

Related U.S. Application Data

[63] Continuation of Ser. No. 294,972, Aug. 24, 1994, Pat. No. 5,628,993.

[30] Foreign Application Priority Data

Aug. 26, 1993 [JP] Japan .................................. 5-235923

[51] Int. Cl.$^6$ .................... A61K 38/02; A61K 38/21; A61K 47/14
[52] U.S. Cl. .................... 424/85.2; 424/85.4; 424/423; 424/468; 514/2; 514/3; 514/786
[58] Field of Search .................... 514/2, 3, 4, 12, 514/21, 786, 964; 424/85.2, 85.4, 85.7, 423, 468, 499, 502

[56] References Cited

U.S. PATENT DOCUMENTS

| | | | |
|---|---|---|---|
| 5,162,057 | 11/1992 | Akiyama et al. | 514/770 |
| 5,189,148 | 2/1993 | Akiyama et al. | 530/399 |
| 5,352,662 | 10/1994 | Brooks et al. | 514/12 |
| 5,628,993 | 5/1997 | Yamagata et al. | 424/85.7 |

FOREIGN PATENT DOCUMENTS

| | | |
|---|---|---|
| 0 246 540 | 11/1987 | European Pat. Off. . |
| 368247 | 5/1990 | European Pat. Off. . |
| 455391 | 11/1991 | European Pat. Off. . |
| 0 514 008 | 11/1992 | European Pat. Off. . |
| 6-219960 | 8/1994 | Japan . |

OTHER PUBLICATIONS

Aggarwal et al., Human Cytokines, Poston: Blackwell Scientific Publications, 1992, pp. 5–9, 20, 32, 33.

*Primary Examiner*—Jeffrey E. Russel
*Attorney, Agent, or Firm*—Foley & Lardner

[57] ABSTRACT

A parenteral pharmaceutical preparation comprises a matrix containing a physiologically active peptide or protein and a polyglycerol diester of a saturated fatty acid, and the matrix is in a solid form at room temperature. The molecular weight of the physiologically active peptide or protein is 2,000 dalton or more. The saturated fatty acid includes fatty acids having about 16 to 30 carbon atoms such as palmitic acid, stearic acid, etc. The matrix may be in a pillar or granular form. The parenteral pharmaceutical preparation can be used as an injectable solid administered subcutaneously or intramuscularly (for example, a pellet or tablet for implantation), a suppository or the like, and can release the physiologically active peptide or protein sustainedly for a prolonged period of one week or more.

16 Claims, No Drawings

SUSTAINED RELEASABLE PARENTERAL PHARMACEUTICAL PREPARATIONS AND METHOD OF PRODUCING THE SAME

This application is a continuation of application Ser. No. 08/294,972, filed Aug. 24, 1994.

FIELD OF THE INVENTION

The present invention relates to a sustained releasable parenteral preparation useful for sustained or prolonged release of a physiologically active peptide or protein, and a method of producing the same.

BACKGROUND OF THE INVENTION

For administration of a therapeutic agent, oral administration is generally employed. Oral administration of a physiologically active peptide or protein, however, causes hydrolysis of the peptide or protein by a digestive enzyme to decrease disadvantageously the absorbability from the digestive tract. Accordingly, such physiologically active peptide or protein is usually administered by repetition of intramuscular or subcutaneous injections or by intravenous drip infusion. These methods, however, are not preferable in a chronic administration, although they are acceptable in a case where the repetition of the injection is extremely limited. By way of illustrating, for the therapy of viral hepatitis type C, interferon-α is continuously administered daily throughout 4 weeks or more (see "Journal of Clinical and Experimental Medicine (IGAKU NO AYUMI)", 161, 5, 359-363 (1992)). In such chronic or frequent administration, however, the patient is obliged to be restrained to a great extent. Therefore, development of an effective and economic administration system for such physiologically active peptide or protein has been demanded.

Japanese Patent Application Laid-open No. 2930/1988 (JP-A-63-2930) discloses a system where a polypeptide is dispersed in a polylactide. Japanese Patent Publication No. 502117/1988 (JP-B-63-502117) and Japanese Patent Application Laid-open No. 234820/1992 (JP-A-4-234820) disclose pharmaceutical preparations using a liposome, and Japanese Patent Publication No. 502574/1991 (JP-B-3-502574) proposes a pharmaceutical preparation where a liposome containing a physiologically active polypeptide is dispersed in a gel.

When these pharmaceutical preparations are administered, however, the drugs are unexpectedly released to a large extent in the initial stage of administration. Thus the drug concentration in blood is increased and the releasing rate of the drug can not be maintained in a certain range. Furthermore, since an organic solvent is used in the manufacture of the preparation, the polypeptide is denaturated to decrease the physiological activity.

Japanese Patent Application Laid-open No. 2930/1988 (JP-A-63-2930) discloses a sustained releasable system for a physiologically active polypeptide, which comprises an atherocollagen-matrix and the physiologically active polypeptide dispersed in the matrix. The atherocollagen used as a base is, however, derived from a foreign or different animal from human being, and it may probably show antigenicity.

Japanese Patent Application Laid-open No. 22012/1988 (JP-A-63-22012) discloses a system prepared by dispersing a physiologically active polypeptide in a water-insoluble matrix and compression-molding the dispersion, as a sustained releasable pharmaceutical preparation for parenteral administration of the polypeptide. The pharmaceutical preparation controls the release of the physiologically active polypeptide by utilizing erosion of the matrix in vivo. Therefore, the polypeptide may be enzymatically degraded or decomposed so as to lower the biological availability.

Japanese Patent Application Laid-open No. 85328/1986 (JP-A-61-85328) discloses a pharmaceutical preparation which comprises a composition of a physiologically active polypeptide and a polyglycerol fatty acid ester, wherein the polyglycerol fatty acid ester is dispersed in water. The pharmaceutical preparation is, however, restricted with regard to a dosage form since it is a solution. Furthermore, since the polyglycerol fatty acid ester is utilized to promote the percutaneous absorption of the physiologically active polypeptide, and the drug can hardly be released for a longer period of time, e.g. for 24 hours or more.

SUMMARY OF THE INVENTION

Accordingly, it is an object of the present invention to provide a sustained releasable parenteral pharmaceutical preparation in which hydrolysis of a physiologically active peptide or protein can be suppressed, the decrease of their activity can be avoided and a sustained release of the peptide or protein can be maintained for a prolonged period.

It is another object of the present invention to provide a sustained releasable parenteral pharmaceutical preparation in which a great release of a physiologically active peptide or protein in an early stage of the administration is suppressed and the peptide or protein can be released for a longer period.

It is yet another object of the invention to provide a sustained releasable parenteral pharmaceutical preparation in which a physiologically active peptide or protein can be released sustainedly for a prolonged period, wherein denaturation of the higher-dimensional structure is suppressed and decrease of the activity of the physiologically active peptide or protein is inhibited.

It is a further object of the invention to provide a sustained releasable parenteral pharmaceutical preparation which does not contain any material causing antigenicity and can release a physiologically active peptide or protein for one week or more.

A yet further object of the present invention is to provide a method of producing a pharmaceutical preparation, by which the pharmaceutical preparation having such excellent characteristics as above can be produced in a simple and easy manner.

After intensive investigation and research to accomplish the above objects, the inventors of the present invention found that a pharmaceutical preparation obtainable by use of specific polyglycerol fatty acid esters selected from numerous polyglycerol fatty acid esters in combination with a physiologically active polypeptide or protein can remarkably improve the sustained release of the physiologically active peptide or protein, and can release the physiologically active peptide or protein sustainedly for a prolonged period. The present invention has been accomplished based on these findings.

Thus, the sustained releasable parenteral pharmaceutical preparation of the present invention comprises a matrix comprising a physiologically active peptide or protein (hereinafter, as far as not particularly mentioned, referred to simply as the physiologically active polypeptide) and a polyglycerol diester of a saturated fatty acid. The average molecular weight of the physiologically active polypeptide may frequently be 2,000 dalton or more, and the diester may be, in many cases, a diester formed with a polyglycerol having an average polymerization degree of about 4 and a saturated fatty acid having 16 to 30 carbon atoms. The matrix may be in a pillar, granular or other form. The matrix may be an injectable solid for implantation.

The sustained releasable pharmaceutical preparation may be prepared by mixing a physiologically active peptide or protein with a molten or softened polyglycerol diester of a saturated fatty acid and molding the molten mixture.

DETAILED DESCRIPTION OF THE INVENTION

In this specification, the term "polyglycerol having an average polymerization degree of 4" means a polymerization degree of polyglycerol as a main compound which is estimated by the terminal analysis of hydroxyl value, and includes tetraglycerol, as well as a mixture of tetraglycerol as a main component and an unavoidable glycerol or glycerol polymer (for example, diglycerol, triglycerol, pentaglycerol, etc.). Therefore, the average polymerization degree of the polyglycerol may be about 3.7 to 4.3.

The term "diester" means the average value of the ester bonds of a main compound which is estimated from the ester value of the polyglycerol fatty acid ester, and includes not only a diester but also a mixture comprising a diester as a main component, and a monoester, a triester which may be coexistent or contaminative unavoidably. Thus, the average value of the ester bond in the diester may be about 1.7 to 2.3.

In cases where the matrix or the polyglycerol diester of a fatty acid is not a single compound but a mixture, the substance does not show a distinct melting point but softens at a specific temperature. The term "melting point" as used in this specification includes, within the meaning thereof, the softening point of such a mixture as well.

As the physiologically active polypeptide in the present invention, various peptides and proteins having physiological activities can be used. The average molecular weight of the physiologically active polypeptide is, for example, about 2,000 dalton or more, preferably about 5,000 to 1,000,000 dalton, more preferably about 10,000 to 500,000 dalton and particularly about 10,000 to 100,000 dalton. Preferred physiologically active polypeptide includes molecules classified into proteins which is expressed as having a higher-dimensional structure in the field of biochemistry.

The physiologically active polypeptide includes classificatorily, for example, proteins, enzymes, nucleoproteins, glycoproteins, lipoproteins, polypeptides having a hormone-like activity, agonists of these molecules, synthetic analogues including antagonists and so on.

The present invention may be applied to a variety of physiologically active polypeptides and the species thereof is not critically restricted. As examples of the physiologically active polypeptides, there may be mentioned immune-controlling factors, lymphokines, monokines, cytokines, enzymes, antibodies, growth stimulating factors, growth suppressing factors, hormones, vaccines (including antigens of viruses, bacteria, parasites and rickettsiae), blood coagulating factors, and various precursor proteins thereof, mutant proteins, and other substances analogous thereto.

To be specified, the physiologically active polypeptide includes, for example, the following physiologically active high molecular compounds, mutant proteins and analogues thereto.

(1) Interferons ($\alpha$-, $\beta$-, $\gamma$-, etc.), interleukins (IL--1, IL-2, IL-3, IL-4, IL-5, IL-6, IL-7, IL-8, IL-9, IL-10, IL-11), antiallergic factors, suppressor factors, cytotoxic glycoproteins, immuno-cytotoxic factors, immuno-toxins, lymphotoxins, tumor necrosis factors (TNF-$\alpha$, TNF-$\beta$, or the like), cachectin, oncostatins, transforming growth factors (TGF-$\alpha$, TGF-$\beta$ and so on), hemopoietic factors (for example, erythropoietin), granulocyte-colony stimulating factor (G-CSF), granulocyte-macrophage colony stimulating factor (GM-CSF), macrophage-colony stimulating factor (M-CSF), macrophage peptides, B-cell factors (e.g. B-cell growth factor, etc.), T-cell factors and so on.

(2) Growth factors, for instance, nerve growth factor (NGF), nerve trophic factor (NTF), polypeptides having actions on cranial nerve cells, epitheliocyte growth factor (EGF), insulin-like growth factor (IGF), growth hormone (GH), fibroblast growth factor (FGF), osteogen growth factor and others. The physiologically active polypeptide belonging to this category further includes, for instance, parathyroid hormone (PTH), endoserine and the like.

(3) Physiologically active polypeptides having a platelet growing action such as platelet-derived growth factor (PDGF), etc.

(4) Physiologically active polypeptides having an enzymatic action including, for instance, factor VIII, factor IX, fibrinolysis factor, tissue plasminogen activator (TPA), urokinase, prourokinase, streptokinase, lipocortin, macrocortin, protein C, C-reactive protein, renin-inhibitor, metalloproteases, tissue inhibitor of metalloprotease (TIMP), superoxide dismutase (SOD) and so on.

(5) Physiologically active polypeptides having a hormone-like action such as insulin, secretin, growth hormone releasing factor (GRF), glucagon, gastrins, prolactin, adrenocorticotropic hormone (ACTH), thyroid-stimulating hormone (TSH), luteinizing hormone (LH), follicle-stimulating hormone (FSH), cholecystokinin, human chorionic gonadotropin (HCG), leukokinin, thymocin, motilin, kallikrein, etc.

(6) Physiologically active polypeptides acting as a vaccine antigen including antigens such as HTLV-I, HTLV-II, AIDS virus group (e.g. HTLV-III/LAV/HIV and HIV-2, etc.), cytomegalovirus, hepatitis A virus, hepatitis B virus, hepatitis C virus, herpes simplex-I virus, herpes simplex-II virus, malaria, larvate rabies retrovirus, infectious gastroenteritis virus, parainfluenza virus, influenza virus, rotavirus group, respiratory syncytial virus, varicella-zoster virus, Epstein-Barr virus, pertussis; and Gram negative bacteria such as Pseudomonas, endotoxins, tetanus toxin, and others. Such physiologically active polypeptide may be administered singly, or bonded with a hapten, or in combination with an adjuvant.

These physiologically active polypeptide may be naturally-occurring, or be prepared by genetic recombination. The physiologically active polypeptide may have a glycosyl chain, and the structure of glycosyl chain may be different. Further, examples of the physiologically active polypeptide include mutants, derivatives, relatives or analogues, or active fragments of the peptides and proteins mentioned above.

The physiologically active polypeptide may be used singly or in combination. A substance which can activate the physiologically active polypeptide and/or other ingredient having arithmetic or synergistic effects with the substance can advantageously be employed in combination with the physiologically active polypeptide. For instance, interferon-$\alpha$ can be used in combination with the activating substance or ingredient such as interleukins, lentinan, minophagen or the like. The activating substance or ingredient may be used singly or in combination, with the physiologically active polypeptide.

The present invention is characterized in that the physiologically active polypeptide is sustainedly releasable for a prolonged period by means of combining specific polyglycerol fatty acid esters among a great number of polyglycerol fatty acid esters.

In the polyglycerol fatty acid ester, the term "polyglycerol" means "a polyhydric alcohol having in each molecule thereof n (when cyclic) to n+2 (when straight-chained or branched) hydroxyl groups, and n−1 (when straight-chained or branched) to n (when cyclic) ether bonds" ["Polyglycerol Ester" edited and published by Sakamoto Yakuhin Kogyo Co., Ltd., Japan; pp 12, (May 2, 1986)]. Polyglycerol can be obtained by dehydrating condensation of glycerol, or recovery from residue of glycerol distillation.

As the component used in combination with the physiologically active polypeptide, a polyglycerol diester of a saturated fatty acid is employed in the present invention. When the fatty acid is an unsaturated fatty acid, the physiologically active polypeptide may be released in an early stage, and the sustained release may be extremely decreased or reduced. Furthermore, even when the compound is an ester formed with a polyglycerol and a saturated fatty acid, a monoester, a triester, a tetraester, a pentaester, or the like may harm or reduce the sustained release of the physiologically active polypeptide remarkably.

Examples of the saturated fatty acid include a saturated fatty acid having 16 to 30 carbon atoms such as palmitic acid, datulic acid, stearic acid, arachic acid, behenic acid, lignoceric acid, cerotic acid, montanic acid, melissic acid and so on. Preferred examples of the saturated fatty acid include a fatty acid having 16 to 22 carbon atoms (for example, palmitic acid, stearic acid, behenic acid, etc.), particularly palmitic acid, stearic acid and the like.

The diesters of these saturated fatty acids may be diester formed with a single fatty acid or with a mixture of two or more of fatty acids.

The polymerization degree of the polyglycerol is not particularly limited to a specific value which does not adversely affect on the sustained releasing properties, and is selected from the range depending on the species of the fatty acid.

Preferred polyglycerol has an average polymerization degree of about 3 to 5, particularly 4. Where the average polymerization degree is less than 3 or more than 5, depending on the species of the saturated fatty acid, the physiologically active polypeptide may be apt to be released or liberated readily, and, in some cases, may hardly be imparted with high sustained releasing properties. Therefore, a polyglycerol having an average polymerization degree of 4 is advisably employed.

The melting point of the polyglycerol diester of the saturated fatty acid is for example about 40° to 60° C., preferably about 42° to 58° C. and more preferably about 45° to 55° C.

The preferred polyglycerol diester of the saturated fatty acid is formed with a polyglycerol having an average polymerization degree of 4 and a saturated fatty acid having 16 to 22 carbon atoms.

Examples of the polyglycerol diester having of the saturated fatty acid includes triglycerol diesters such as triglycerol dipalmitate, triglycerol distearate and triglycerol dibehenate; tetraglycerol diesters such as tetraglycerol dipalmitate, tetraglycerol didatulate, tetraglycerol distearate, tetraglycerol diarachate, tetraglycerol dibehenate, tetraglycerol dilignocerate, tetraglycerol dicerotate, tetraglycerol dimontante, tetraglycerol dimelissate, tetraglycerol monopalmitate monostearate, tetraglycerol monopalmitate monobehenate and tetraglycerol monostearate monobehenate; pentaglycerol diesters such as pentaglycerol dipalmitate, pentaglycerol distearate, pentaglycerol dibehenate and the like. Preferred examples of the diester include tetraglycerol diesters such as tetraglycerol dipalmitate, tetraglycerol distearate, tetraglycerol dibehenate and others. These diesters can be employed independently or in combination.

The polyglycerol diester is usable for an emulsifier as a food additive, and the safety in vivo has already been confirmed. Further, the diester may finally be absorbed in vivo and moreover presents no antigenicity.

Matrixes comprising a polyglycerol higher fatty acid ester and a peptide or protein are disclosed in Japanese Patent Application Laid-open No. 223533/1990 (JP-A-2-223533), EP-A 443572, Japanese Patent Application Laid-open Nos. 237/1993 (JP-A-5-237) and 132416/1993 (JP-A-5-132416). However, these prior literatures do not disclose that a matrix comprising a combination of a polyglycerol diester of the saturated fatty acid and a physiologically active polypeptide can release the physiologically active polypeptide for an extremely prolonged time period.

The pharmaceutical preparation of the present invention is composed of a matrix comprising the physiologically active polypeptide and the diester. Usually, preferred preparation is formed with a matrix wherein the physiologically active polypeptide is dispersed in the diester. The matrix is preferably in a solid form at room temperature or ambient temperature (5° C. to 35° C.), and, usually, the physiologically active polypeptide is homogeneously dispersed in the diester. When the physiologically active polypeptide is dissolved in the molten diester in the manufacturing procedure, it is preferable to mix homogeneously to give a pharmaceutical preparation where the polypeptide is dispersed in a solid form at room temperature. Such pharmaceutical preparation is characterized by suppressing the release of the physiologically active polypeptide in the early stage of the administration to a great extent, and sustainedly or continuously releasing of the peptide for a prolonged time period with maintaining the higher-dimensional structure thereof.

The ratio of the physiologically active polypeptide relative to the diester can be selected from a wide range, and the proportion of the physiologically active polypeptide in the matrix composed of the two components is, for instance, about 0.0001 to 50% by weight, preferably about 0.001 to 20% by weight and more preferably about 0.001 to 10% by weight, and the residue is formed with the diester.

The matrix may be added, if required, with an ingredient commonly used in the field of solid pharmaceutical preparations such as an excipient, a binder and a disintegration agent, as well as various additives such as a stabilizing agent, a preservative and the like. Examples of the stabilizing agent include gelatin, albumin, globulin, protamine, trehalose, D-glucose, dextran and others. As the preservative, there may be mentioned, for instance, paraoxybenzoic acid esters (for example, methylparaben, propylparaben, etc.), benzyl alcohol, chlorobutanol, thimerosal and so on.

The sustained releasable parenteral pharmaceutical preparation may be in any form so far as to be administered parenterally or non-orally, and is, usually, formed with a matrix in such a dosage form that will not give a patient an excessive pain or suffering, for example, a small or compact matrix. A characteristic of the present invention is that even such small or compact matrix as to be administrable by means of, for instance, a needle for injection, the physiologically active polypeptide can be released sustainedly for a prolonged period. By way of illustration, non-oral administration of the present pharmaceutical preparation can prolong the period of the physiologically active polypeptide in blood, for instance, 7 days or more, in comparison with a single or separate administration of the physiologically active polypeptide. Thus, the dosage time of the preparation and pain or suffering given to the patient can extremely be reduced.

The pharmaceutical preparation may be utilized as, for instance, an injectable solid which is administrable subcutaneously or intramuscularly (e.g. a pellet or implant, etc.), or a transmucosally absorbable composition such as a suppository. The shape or form of the preparation can be selected from a range depending on the dosage form, and may, for instance, be in a powdery or granular form as a powder, a granule or a pill; in a flat, ellipse, rod or pillar form as an injectable pellet or tablet for implantation; or in a spherical or oval form as a suppository. When used as an injection, the preparation may frequently be in a pillar or powdery form. Preferred form of the pharmaceutical preparation includes, for instance, pillar form such as cylindrical or columnar form and granular form such as spherical form.

The size of the parenteral or non-oral pharmaceutical preparation of the present invention may also be selected according to the dosage form, as far as it will not pain a patient to an excessive extent. For an injection, when the preparation is a pillar-formed matrix, the size is for example about 3 mm or less in diameter and about 30 mm or less in length, preferably about 1 mm or less in diameter and about 20 mm or less in length which can be administered by using a needle of 11 G or less, more preferably about 0.1 to 1 mm in diameter and about 1 to 20 mm in length, and practically preferred is in a cylindrical or columnar form. The grain or particle size of an injectable granular matrix is, in maximum diameter, about 1 mm or less, preferably about 150 µm or less and more preferably about 1 to 100 µm. The weight of the matrix may be chosen depending on the form or shape of the pharmaceutical preparation, and is usually, for example, about 40 mg or less and preferably about 1 to 25 mg for an injection.

The pharmaceutical preparation of the present invention can be prepared by various methods, and the preferred is such that using no organic solvent which denatures the polypeptide. As such a method, there may be mentioned, for instance, a process which comprises mixing a physiologically active polypeptide to a molten or softened polyglycerol diester of the saturated fatty acid, and molding the resultant molten mixture into a preparation. Although the physiologically active polypeptide is thermodynamically unstable in an aqueous solution, it is unexpectedly stable in a solid form such as a freeze-dried powder. Therefore, the physiologically active polypeptide in a solid powdery or granular form such as a dried powder is preferably used for homogeneous mixing.

In the molding, any molding method can be employed according to the form or shape of the pharmaceutical preparation. For instance, an injection can be prepared by sucking up the molten mixture into a syringe with a needle and extruding the charged from the needle to give a pillar product or by dropping the molten mixture onto a rotary plate or disk and centrifuging or tumbling the droplets to obtain a spherical product. Further, a fine particulate pharmaceutical preparation can be produced by atomizing or spraying the molten mixture and chilling the powdery product, or by subjecting the shaped product such as a pellet to a pulverizing means such as a jet mill to obtain a fine particle.

The following examples and experimental example are merely intended to illustrate the present invention in further detail and should not be construed as defining the scope of the invention.

EXAMPLES

Example 1

Tetraglycerol dipalmitate (300 mg; the number of ester bond: 2.0; manufactured by Sakamoto Yakuhin Kogyo Co., Ltd., Japan) was heated at 48° C. for melting, and was added with 7.2 mg of a freeze-dried powdery interferon-α. A part of the molten mixture was sucked up into a needle of 11 G by use of a syringe, cooled at room temperature and the charged was extruded from the needle to give a cylindrical matrix pharmaceutical preparation (1 mm in diameter, 10 mm in length, about 10 mg in weight).

Example 2

Tetraglycerol distearate (300 mg; the number of ester bonds: 2.0; manufactured by Sakamoto Yakuhin Kogyo Co., Ltd., Japan) was heated at 58° C. for melting, and to the molten was added 7.2 mg of a freeze-dried powder of interferon-α. A portion of the molten mixture was sucked up into a needle of 11 G by use of a syringe and was cooled at room temperature. The charged was extruded to give a cylindrical matrix pharmaceutical preparation (1 mm in diameter, 10 mm in length, about 10 mg in weight).

Example 3

A molten mixture of tetraglycerol dipalmitate and the freeze-dried powdery interferon-α was prepared in the same manner as in Example 1. The molten mixture was sucked up into a 1 ml-syringe (Terumo Co., Ltd., Japan), and, with maintaining the temperature at 50° C., the matrix was sprayed or atomized with an air gun (Hakuko Co., Ltd., Japan) with extruding from a needle of 27 G (Terumo Co., Ltd., Japan) to give microspheres. The microspheres were passed through a sieve (16 mesh) to remove granular products having a diameter of 1 mm or more.

Example 4

After heated at 48° C. for melting, the molten tetraglycerol dipaimitate (300 mg; Sakamoto Yakuhin Kogyo Co., Ltd., Japan) was added with 1.5 mg of a freeze-dried powder of interleukin-2. A portion of the molten mixture was sucked up to a needle of 11 G with a syringe, cooled at room temperature and extruded the charged from the needle to obtain a cylindrical matrix pharmaceutical preparation having a diameter of 1 mm, a length of 20 mm and a weight of about 20 mg.

Example 5

Tetraglycerol dipalmitate (300 mg; Sakamoto Yakuhin Kogyo Co., Ltd., Japan) was heated at 48° C. for melting, and to the molten was added 1.5 mg of a freeze-dried powder of insulin. The molten mixture was sucked up into a needle of 11 G by use of a syringe and cooled at room temperature. The charged was extruded from the needle to give a cylindrical matrix pharmaceutical preparation (1 mm in diameter, 20 mm in length, about 20 mg in weight).

Comparative Example 1

A cylindrical matrix pharmaceutical preparation (1 mm in diameter, 10 mm in length, about 10 mg in weight) was obtained in the same manner as in Example 1 except for using glycerol monopalmitate (the number of ester bond: 1.0; Riken Vitamin Co., Ltd., Japan) instead of tetraglycerol dipalmitate.

Comparative Example 2

The procedures of Example 1 was followed by using diglycerol monopalmitate (the number of ester bond: 1.0; Sakamoto Yakuhin Kogyo Co., Ltd., Japan) instead of tetraglycerol dipalmitate to give a cylindrical matrix pharmaceutical preparation having a diameter of 1 mm, a length of 10 mm and a weight of about 10 mg.

Comparative Example 3

A cylindrical pharmaceutical preparation (1 mm in diameter, 10 mm in length, about 10 mg in weight) was prepared in the same manner as in Example 2 except for using glycerol monostearate (the number of ester bond: 1.0; Takeda Chemical Industries, Ltd., Japan) instead of tetraglycerol distearate.

Comparative Example 4

The procedure of Example 2 was repeated except for using diglycerol monostearate (the number of ester bond: 1.0; manufactured by Sakamoto Yakuhin Kogyo Co., Ltd., Japan) in place of tetraglycerol distearate to obtain a cylindrical matrix pharmaceutical preparation having a diameter of 1 mm, a length of 10 mm and a weight of about 10 mg.

Comparative Example 5

A cylindrical pharmaceutical preparation (1 mm in diameter, 10 mm in length and about 10 mg in weight) was prepared by the same procedure as in Example 2 except for using tetraglycerol monostearate (the number of ester bond: 1.0; Sakamoto Yakuhin Kogyo Co., Ltd., Japan) instead of tetraglycerol distearate.

Comparative Example 6

Using tetraglycerol tristearate (the number of ester bond: 3.0; manufactured by Sakamoto Yakuhin Kogyo Co., Ltd., Japan) instead of tetraglycerol distearate, the procedures of Example 2 was followed to give a cylindrical pharmaceutical preparation (1 mm in diameter, 10 mm in length, about 10 mg in weight).

Example 6

A cylindrical pharmaceutical preparation (1 mm in diameter, 10 mm in length, about 10 mg in weight) was prepared in the same manner as in Example 2 except for using tetraglycerol dimyristate (the number of ester bond: 2.0; Sakamoto Yakuhin Kogyo Co., Ltd., Japan) instead of tetraglycerol dipalmitate.

Experimental Example

The matrix pharmaceutical preparations obtained in Examples 1 and 2 and Comparative Examples 1 to 6 were respectively administered to a male JCL-SD rat (aged: 6 weeks) subcutaneously in the back in a dose of 10 mg by using a needle of 11 G with a syringe. Each cylindrical matrix pharmaceutical preparation contains $4 \times 10^7$ International Unit (IU) of interferon-$\alpha$.

As a control run, an aqueous solution containing $4 \times 107$ IU of interferon-$\alpha$ was used.

After administration, 0.6 ml of blood was corrected from the tail vein with the lapse of time to obtain serum samples. The serum samples were taken respectively from three rats, and the concentration of interferon-$\alpha$ in each serum sample was determined by sandwich ELISA using two species of anti-interferon-$\alpha$ antibodies, and the average value was calculated. As the unit of standard interferon-$\alpha$, Canferon-TM (Takeda Chemical Industries, Ltd., Japan) was employed. The average values of interferon-$\alpha$ concentration in the serums with the passage of time after administration are set forth in Tables 1 and 2.

In Tables 1 and 2, the term "ND" means "not detectable".

TABLE 1

| Time course after administration (hr) | Interferon Concentration in Serum (IU/ml) | | | | |
|---|---|---|---|---|---|
| | Ex. 1 | Ex. 2 | Comp. Ex. 1 | Comp. Ex. 2 | Comp. Ex. 3 |
| 0.25 | — | — | — | — | — |
| 0.5 | — | — | — | — | — |
| 1.0 | 2086.4 | 2717.9 | 7544.1 | 5712.4 | 7790.5 |
| 2.0 | 2394.1 | 4366.2 | 10692.8 | 13973.0 | 15576.8 |
| 4.0 | 3753.5 | 3088.6 | 7021.8 | 12734.9 | 10122.6 |
| 6.0 | 3380.1 | 2233.9 | 7555.4 | 15510.4 | 8134.6 |
| 8.0 | — | — | — | — | — |
| 24.0 | 1651.3 | 1235.0 | 1666.8 | 3312.3 | 2586.5 |
| 48.0 | 1196.4 | 810.3 | 315.0 | 1374.4 | 664.2 |
| 78.0 | 913.7 | 421.1 | — | 597.1 | 205.5 |
| 102.0 | — | — | 12.5 | — | — |
| 120.0 | 636.3 | 365.5 | ND | 60.5 | 42.6 |
| 144.0 | 509.4 | 184.7 | | 41.8 | 10.8 |
| 168.0 | 629.0 | 304.0 | | ND | ND |
| 192.0 | 568.1 | 777.4 | | | |
| 216.0 | 243.0 | 612.5 | | | |
| 288.0 | 11.8 | 43.4 | | | |

TABLE 2

| Time course after administration (hr) | Interferon Concentration in Serum (IU/ml) | | | |
|---|---|---|---|---|
| | Comp. Ex. 4 | Comp. Ex. 5 | Comp. Ex. 6 | Control |
| 0.25 | — | — | — | 29991.7 |
| 0.5 | — | — | — | 44498.1 |
| 1.0 | 12288.5 | 6521.3 | 2058.2 | 52899.6 |
| 2.0 | 19530.8 | 14726.3 | 959.7 | 51446.0 |
| 4.0 | 10826.0 | 18105.3 | 582.6 | 17055.2 |
| 6.0 | 8680.0 | 17533.5 | 585.8 | 3770.4 |
| 8.0 | — | — | — | 1041.8 |
| 24.0 | 1932.5 | 2605.2 | 58.8 | 117.7 |
| 48.0 | 492.0 | 99.5 | 38.9 | ND |
| 78.0 | — | 43.3 | 11.3 | |
| 120.0 | 43.3 | ND | ND | |
| 144.0 | ND | | | |
| 168.0 | | | | |
| 192.0 | | | | |
| 216.0 | | | | |
| 288.0 | | | | |

An apparent from Tables 1 and 2, the pharmaceutical preparations of Example 1 and Example 2 respectively obtained by using tetraglycerol dipalmitate and tetraglycerol distearate among polyglycerol higher fatty acid esters can sustainedly release interferon-$\alpha$ for one week or more, and the releasing period of interferon-$\alpha$ is longer than the pharmaceutical preparations of Comparative Examples by a factor of 2 or more.

What is claimed is:

1. A method for treating or preventing diseases in a subject for which a physiologically active peptide or protein is effective, which method comprises administering by injection or implantation to the subject a sustained releasable pharmaceutical preparation comprising a matrix containing an effective amount of the physiologically active peptide or protein and a polyglycerol diester of a saturated fatty acid.

2. A method according to claim 1, wherein the polyglycerol has an average polymerization degree of 4.

3. A method according to claim 1, wherein the saturated fatty acid has 16 to 30 carbon atoms.

4. A method according to claim 1, wherein the polyglycerol has an average polymerization degree of 4 and the saturated fatty acid has 16 to 30 carbon atoms.

5. A method according to claim 1, wherein said physiologically active peptide or protein is dispersed in said diester.

6. A method according to claim 1, wherein the physiologically active peptide or protein has an average molecular weight of 2,000 dalton or more.

7. A method according to claim 1, wherein the physiologically active peptide or protein is an interferon, an interleukin or insulin.

8. A method according to claim 1, wherein said saturated fatty acid has 16 to 22 carbon atoms.

9. A method according to claim 1, wherein said saturated fatty acid is palmitic acid or stearic acid.

10. A method according to claim 1, wherein the proportion of the physiologically active peptide or protein is 0.0001 to 50% by weight based on the matrix.

11. A method according to claim 1, wherein said matrix is in a pillar or granular form.

12. A method according to claim 1, wherein said matrix is an injectable solid for implantation.

13. A method according to claim 1, wherein said sustained releasable pharmaceutical preparation comprises a matrix comprising a physiologically active peptide or protein having an average molecular weight of 5,000 to 1,000,000 dalton and a diester of a polyglycerol having an average polymerization degree of 4 and a saturated fatty acid having 16 to 22 carbon atoms, wherein the matrix is administrable subcutaneously or intramuscularly and 0.001 to 20% by weight of the physiologically active peptide or protein based on the matrix is dispersed in the diester.

14. A method according to claim 13, wherein said saturated fatty acid is palmitic acid, stearic acid or behenic acid.

15. A method according to claim 13, wherein said diester has a melting point of 40° to 60° C. and said matrix is in a solid form at room temperature.

16. A method according to claim 13, wherein said physiologically active peptide or protein is an interferon.

* * * * *

UNITED STATES PATENT AND TRADEMARK OFFICE
CERTIFICATE OF CORRECTION

PATENT NO. : 5,750,100
DATED : May 12, 1998
INVENTOR(S) : Yutaka YAMAGATA et al.

It is certified that error appears in the above-identified patent and that said Letters Patent is hereby corrected as shown below:

On the title page, item [30]
Foreign Application Priority Data, delete "5-235923" and insert --5-235823--.

Signed and Sealed this

Twelfth Day of January, 1999

Attest:

Attesting Officer          Acting Commissioner of Patents and Trademarks